United States Patent [19]

Bruce et al.

[11] Patent Number: 5,015,256
[45] Date of Patent: May 14, 1991

[54] METHOD AND MEANS FOR FIXING A JOINT PROSTHESIS

[75] Inventors: Ingrid Bruce; Lars Burce, both of Viken, Sweden

[73] Assignee: AB Idea, Sweden

[21] Appl. No.: 411,511

[22] PCT Filed: Mar. 30, 1988

[86] PCT No.: PCT/SE88/00157
§ 371 Date: Nov. 16, 1989
§ 102(e) Date: Nov. 16, 1989

[87] PCT Pub. No.: WO88/07355
PCT Pub. Date: Oct. 6, 1988

[30] Foreign Application Priority Data

Mar. 30, 1987 [SE] Sweden .................... 8701313

[51] Int. Cl.⁵ .................... A61F 2/30; A61F 2/32
[52] U.S. Cl. .................... 623/18; 623/23
[58] Field of Search .................... 623/16–23, 623/66

[56] References Cited

U.S. PATENT DOCUMENTS

| | | | |
|---|---|---|---|
| 3,918,100 | 11/1975 | Shaw et al. | 623/18 |
| 4,277,238 | 7/1981 | Katagiri | 623/16 |
| 4,497,075 | 2/1985 | Niwa et al. | 623/18 |
| 4,535,485 | 8/1985 | Ashman | 623/16 |
| 4,612,160 | 9/1986 | Donlevy et al. | 623/16 |
| 4,644,942 | 2/1987 | Sump | 623/18 |
| 4,705,519 | 11/1987 | Hayes et al. | 623/66 |
| 4,713,076 | 12/1987 | Draenert | 623/16 |
| 4,718,909 | 1/1988 | Brown | 623/16 |

FOREIGN PATENT DOCUMENTS 2305441  8/1974  Fed. Rep. of Germany ........ 623/18

*Primary Examiner*—David J. Isabella
*Attorney, Agent, or Firm*—Bacon & Thomas

[57] ABSTRACT

A method for fixing a joint prosthesis having an outer friction surface includes reaming a cavity in bone structure in which the prosthesis is to be applied and filling the cavity with grains of biologically compatible material. The stem of the prosthesis is driven down into the grain bed until it is substantially surrounded by the grains. The grains are subjected to an external force so that locking and compaction of the grains with respect to each other, and with respect to the prosthesis stem and bone tissue, is brought about. Preferably, the grains are irregular and/or plastic, having a particle size smaller than 5 mm, preferably between 0.5 and 2 mm. The prosthesis stem preferably is driven down into the grain bed by subjecting the grains, via the prosthesis, to vibrations of such a frequency that they are caused to fluidize. After the prosthesis stem is set in the grains, the grains may thereafter be subjected to vibrations of a different frequency so that locking and compaction of the grains with respect to each other and with to the prosthesis stem and the bone tissue is brought about.

15 Claims, 1 Drawing Sheet

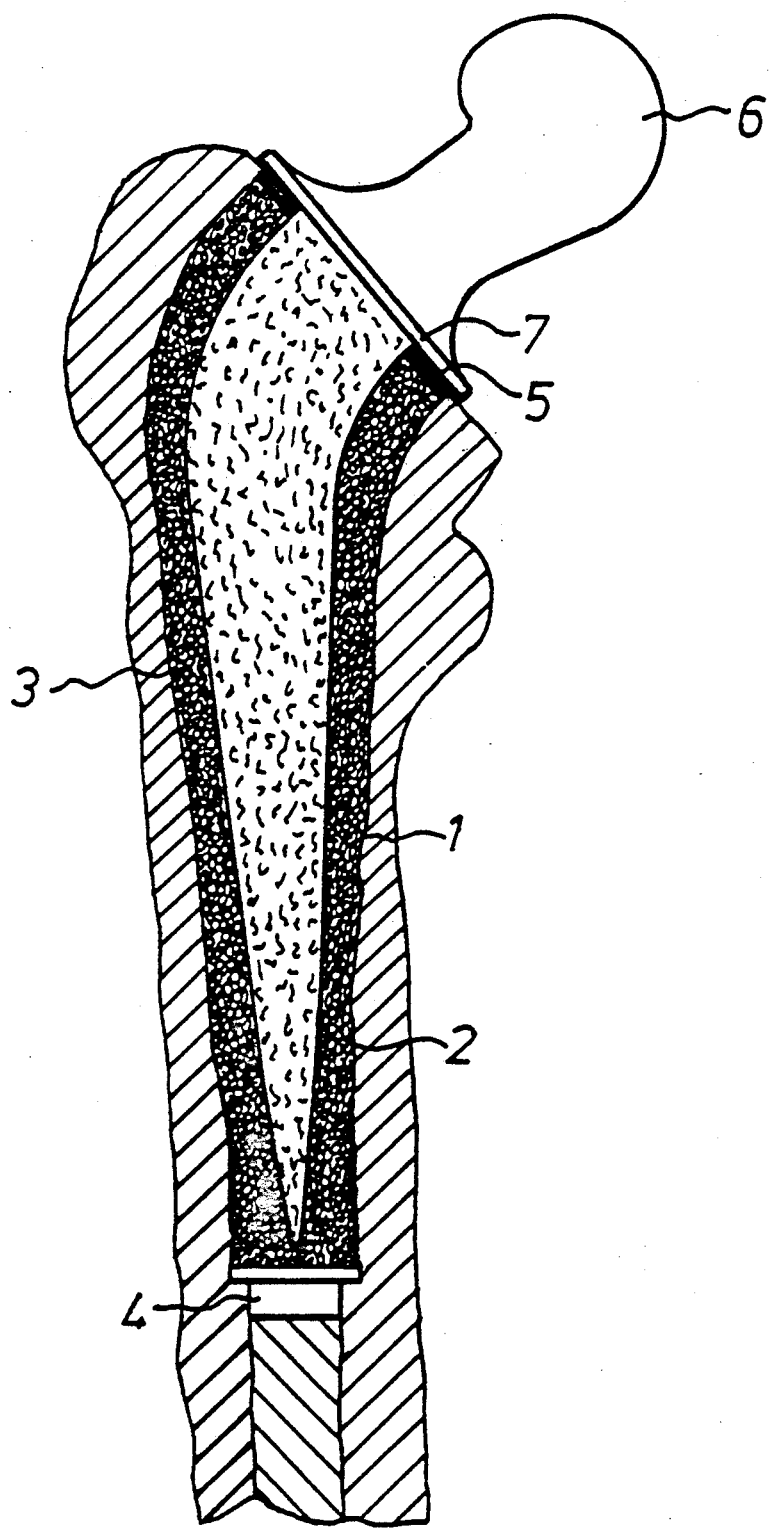

METHOD AND MEANS FOR FIXING A JOINT PROSTHESIS

BACKGROUND OF THE INVENTION

1. Field of the Invention

The present invention relates to a method and means for fixing joint prostheses.

2. Related Art and Technology

A common method of anchoring a joint prosthesis is cementing it to bone tissue, i.e. filling a gap between the joint prosthesis and the osseous wall with bone cement. The problem of unsatisfactory long-term fixation of cemented prostheses has resulted in that use is now less frequently made of cement for fixing prostheses. In this context, it is vital that the shape of the prosthesis stem, which is inserted in the cavity reamed in the bone, conforms well with the shape of the cavity, and that the bridging distance between the osseous wall and the surface of the prosthesis stem is as short as possible to allow bone tissue to form and, within a reasonable time, grow onto the prosthesis from all sides to anchore it to the osseous wall. The minimum bridging distance is of course a true physical contact between the prosthesis surface and the osseous wall but, in a joint prosthesis in a bone, it is highly unlikely that such contact can be established other than at points, which is not sufficient. It is difficult to combine the cementless method, consisting in establishing such a physical contact and providing good long-term fixation but poor short-term fixation, with the method using bone cement which provides good short-term fixation but poor long-term fixation, since the bone cement isolates the prosthesis surface from the osseous wall.

BRIEF SUMMARY OF THE INVENTION

According to the invention, the fixation of the joint prosthesis to bone tissue is ensured by means of a biologically compatible, granular material in which the grains have a substantially even particle size distribution and are substantially irregular and/or plastic. After the operation is completed, these grains should be tightly packed and locked relative to each other and to the bone tissue and the prosthesis stem. By using grains as anchoring means, larger tolerances between the prosthesis stem and the osseous wall are permissible as compared with conventional cementless operations, the problems linked with the use of bone cement being at the same time eliminated. Thus, the present invention offers a solution to the problem of achieving good short-term fixation as well as good long-term fixation.

In practice, the fixation of the prosthesis can be achieved in different ways.

Preferably, the method according to the invention is carried out in the following way.

A cavity is reamed in the bone in which the prosthesis is to be applied. Grains of biologically compatible material are placed in the cavity so as to form a bed, whereupon the prosthesis is driven down into the grain bed until substantially the entire prosthesis stem is surrounded by the grains. A device for retaining the grains is applied around the prosthesis stem, and the prosthesis is finally fixed, optionally by striking it with a tool.

More specifically, the mixture of grains is first inserted in the cavity so as to substantially fill the cavity as a bed of grains. The grain bed should reach substantially up to the resection surface. The distal end of the prosthesis stem is thereafter inserted in the bed, and the grains are subjected, by a striking force exerted on the prosthesis, to vibrations of such a frequency that the grains are caused to fluidize. While the grains are fluidized, the stem is driven down into the bed, substantially to its intended final position. The grains in the bed are thereafter subjected to vibrations of such a second frequency that packing, i.e. interlocking and compaction, of the grains with respect to each other, and of the grains with respect to the prosthesis stem and the bone tissue is brought about.

After said interlocking and compaction step, the prosthesis may optionally be finally fixed by strokes exerted on the prosthesis in the longitudinal direction thereof.

According to an advantageous and preferred aspect of the invention, said cavity has as lower boundary a stop plug which is passed down through the cavity and which may serve as an abutment to the stresses deriving from the above-mentioned striking/driving-down forces.

Alternatively, the grain mixture can be inserted in the cavity after the prosthesis stem, here being conically tapering, has been inserted in the cavity. In this case, the prosthesis stem thus is first inserted in the cavity so as to leave a gap between the boundary wall of the cavity, which consists of bone tissue, and the outer friction surface of the prosthesis stem. The grain mixture is thereafter inserted in said gap, substantially up to the level of the resection surface. The compaction step is thereafter carried out by striking one or more times on the head of the stem. In this manner, the grains will be wedged with respect to each other, i.e. packed in said gap, thus bringing about said compaction and interlocking.

As earlier mentioned, the method according to the invention uses prostheses the stems of which have an outer friction surface which is adapted, after the operation is completed, to ensure mechanical locking between the prosthesis stem and the grains. The outer friction surface is formed with irregularities or unevennesses which may, but need not necessarily, be of substantially the same size as the grains. The shape of the outer friction surface is not critical as long as the grains can engage the unevennesses thereon. Corresponding interlocking between the grains and the osseous wall is obtained since the osseous wall will have unevennesses which result from the reaming operation and in which the grains can engage.

The engagement between the outer surface of the stem and the grains, between the different grains, and between the grains and the bone tissue is enhanced if the stem, after the vibration step, is subjected to the optional final fixing stroke/strokes. In this way, the grains adjacent the bone tissue will penetrate, if they have not previously done so during the locking and compaction step, deep into the osseous wall and into engagement with the outer surface of the stem.

In order to make it easier to drive the prosthesis down into the grain bed, the distal end of the prosthesis stem is suitably pointed, and the prosthesis stem is conically tapering towards its distal end.

The grains which are used in the method according to the invention must satisfy certain requirements to give a satisfactory result of the surgical operation. Thus, the grains must consist of biologically compatible material. One example of such materials primarily is titanium (having, after oxidation in air, an outer layer of titanium dioxide). Other suitable materials are tantalum, niobium and alloys thereof, like titanium alloys. So-called bioceramics, such as $Al_2O_3$, bioglass and hydroxyapatite, can also be used. Grains of other materials which have been surface-coated with layers of biologically compatible material, preferably titanium, may of course also be used. Further, the grain mass may consist wholly or partly of grains of body-endogenous material, such as ground bone tissue.

As mentioned above, the grain mixture applied in the cavity is a substantially homogenous mixture. The grains should have a substantially even particle size distribution such that, when it comes to interlocking and compaction by vibration, no stratification in different particle sizes should occur in the cavity with a consequent risk of uneven and impaired bone ongrowth. The term "substantially even particle size distribution" as used herein means that the "particle diameter" may vary by $\pm 50\%$, preferably $\pm 25\%$ or less. The absolute grain size may vary within relatively wide ranges, a particle size of below about 5 mm being regarded as optimal. The lower limit may be difficult to set. Very small grain particles might be usable in combination with a biologically compatible liquid binding the small grain particles (the fines). Normally, use is however made of grain particles of sizes above 0.1 mm. Preferably, the upper limit may be at about 2 mm and the lower limit at about 0.5 mm. Generally speaking, the particle size is selected with regard to the space which, after the operation is completed, should be packed with grains, i.e. coarser particles are thus normally chosen e.g. for hip-joint operations, while smaller particle sizes are used e.g. for finger-joint operations.

In order to provide total interlocking, i.e. locking of osseous wall to grains, grains to grains, grains to prosthesis stem, the grains should further be irregular and/or plastic, i.e. be able to change their shape when subjected to an external force and to maintain the new shape when the external force has ceased to act. Although it is possible to use solid grains, grains having a certain, preferably high porosity are preferred. Porous grains are obtained in a known manner by blowing gas or liquid through a melt of granular material. Optionally, the grains may be charged or coated with antibiotics and/or growth-stimulating agents.

In the preferred embodiment described above, the grains are fluidized in the grain bed in order to allow the prosthesis stem to be driven down into the grain bed in the reamed cavity. Fluidization is carried out in two steps, the first at a high frequency allowing the prosthesis stem to be driven down into the grain bed in that the grains of the bed placed in the cavity behave as a liquid. This first fluidization step is followed by fluidization at a lower frequency providing room for the grains in the bed between each other so as to be wedged with respect to each other, thus bringing about compaction and interlocking. Suitable frequencies for the vibrations required for fluidization, compaction and interlocking can easily be tested out in each special case by anyone of ordinary skill in the art and depend on factors, such as type of grains and type of prosthesis. Good results have been achieved when using a pneumatically powered, oscillating bone saw of conventional type and here provided with gripping means, in the case of porous titanium powder having a particle size of between 1 and 1.5 mm.

The grain mass is fixed in the cavity by applying, around the prosthesis stem, a collar or ring of bone cement or plastic above the resulting, compacted, interlocking bed of grains. Alternatively, bone cement or an equivalent quick-setting liquid may be poured over the grains.

The prosthesis (prosthesis stem) may be of a per se known type, as long as it has an outer, e.g. rough or uneven friction surface. Suitably, the stem consists of a biologically compatible, growth-stimulating material or has a surface layer of such a material, thus forming said outer friction surface.

DESCRIPTION OF THE DRAWINGS

In the enclosed drawing, there is shown a hip-joint prosthesis which has been fixed by the method and the means according to the present invention.

DETAILED DESCRIPTION OF PREFERRED EMBODIMENT

The space between an osseous wall 1 and the outer wall 2 of the conical stem of a hip-joint prosthesis is filled with irregular grains 3 of pure titanium having a size of about 1 mm. The grains 3 are porous and have been obtained by blowing gas through a melt of the granular material. The grains are packed and wedged with respect to each other. Mechanical interlocking is provided between the stem outer wall 2 and the grains adjacent thereto as well as between the osseous wall 1 and the grains adjacent thereto. A "bottom plug" 4, which advantageously consists of a piece of the patient's own hip-joint ball earlier removed by surgical operation, forms a lower boundary of the cavity and engages the surrounding osseous wall by a flange. A cover 5 of bone cement forms an upper boundary of the cavity. In the drawing, the thickness of the grain layer is exaggerated for greater clarity.

The above-mentioned compaction, interlocking and wedging and, consequently, prosthesis fixation is brought about in the following way.

After the surgeon in a traditional manner has reamed the part of the femur in which the prosthesis stem should be implanted, and applied the bottom plug 4, the resulting cavity is filled with said grains 3, sterilized e.g. by autoclaving, up to a level slightly below the opening of the reamed bone. The prosthesis stem is thereafter inserted in the thus obtained grain bed and driven into it so far that only a few mm remain between the collar 7 and the opening of the bone. For driving the prosthesis stem into the bed of grains, use is made of a vibrating tool with adjustable frequency, acting on the head 6 of the prosthesis stem and adapted, at a suitable vibration frequency, to loosen the grain bed, thus allowing the stem to penetrate into the bed. If the penetration of the stem into the bed becomes excessively slow because of the compactness of the bed, the surgeon increases the vibration frequency. Once a position of the prosthesis stem has been obtained as defined above, the grains are subjected to such a treatment that they will settle in a manner to be compacted and locked to each other. This is preferably done by subjecting the prosthesis stem, by means of the vibrating tool, to a progressively decreasing vibration frequency, by strokes on the prosthesis stem or otherwise.

Bone cement is now applied in a ring around the stem below the collar 7, whereupon the stem is completely driven down into the grain bed by striking with a hammer. This measure enhances the previously mentioned interlocking, wedging and application/penetration effects. The bone cement in the ring can now be cured so as to form the cover 5.

It has been found that the initial vibration of the stem most suitably is a reciprocating movement along an approximately horizontal circular arc. This vibration causes the grains 3 in the stem cavity to float and makes it possible to rapidly drive the stem into the bed.

Although the invention is described with reference to hip-joint prostheses, it is evident to anyone skilled in the art that the means and the method of the invention are applicable also to other types of prostheses.

We claim:

1. A method for fixing a joint prosthesis in a bone cavity comprising the steps of:
    reaming a cavity in a bone;
    filling the cavity with grains of biocompatible material forming a grain bed;
    inserting a stem portion of the prosthesis into the grain bed until the entire stem is substantially surrounded by the grains;
    applying an external compaction force to the grain bed thereby securably locking the prosthesis in the cavity; and
    applying a retaining device to the bed for retaining the grains within the cavity.

2. The method as claimed in claim 1, wherein, before filling the cavity with said grains, a stop plug is positioned in a distal portion of the cavity.

3. The method as claimed in claim 1, wherein the prosthesis is driven to a final fixed position by applying force to the prosthesis along its longitudinal axis.

4. The method as claimed in claim 1, wherein the prosthesis stem is driven down into the grain bed by subjecting the grains, via the prosthesis, to vibrations of such a frequency that they are caused to fluidize, the prosthesis penetrating down into said cavity until substantially the entire prosthesis stem is surrounded by the grains.

5. The method as claimed in claim 4, wherein, after said prosthesis stem is substantially surrounded by the grains, the grains are thereafter subjected, via the prosthesis, to vibrations of such a different frequency that locking the compaction of the grains with respect to each other, and with respect to the prosthesis stem and the bone tissue, is brought about.

6. A method for fixing a joint prosthesis having an outer friction surface, comprising the steps of:
    reaming a cavity in the bone in which the prosthesis is to be applied;
    applying a stop plug in the bottom of the resulting cavity;
    inserting a stem of a prosthesis in said cavity;
    inserting irregular grains of a biologically compatible material in substantially the entire space formed between the prosthesis and the surrounding bone tissue;
    applying a device for retaining the grains around the prosthesis stem; and
    fixing the prosthesis in the cavity by a stroke or strokes applied to the prosthesis in the insertion direction.

7. A method for fixing a joint prosthesis as claimed in claim 6, wherein the grains, via the prosthesis, are subjected to vibrations of such a frequency that the grains are locked and compacted with respect to each other, and with respect to the prosthesis stem and the bone tissue.

8. A method as claimed in claim 1, wherein the step of filling the cavity with grains includes using irregular grains.

9. A method as claimed in claim 1, wherein the step of filling the cavity with grains includes using plastic grains.

10. A method as claimed in claim 8, including using grains having a particle size between 0.5 and 5 mm.

11. A method as claimed in claim 10, wherein the size of the grains used is between 0.5 and 2 mm.

12. A method as claimed in claim 1, wherein the step of filling the cavity with grains includes using grains selected from the group consisting of titanium/titanium oxide, tantalum, niobium and alloys thereof, and bioceramic material.

13. A method as claimed in claim 1, wherein the step of filling the cavity with grains includes using grains of body-endogenous material such as, for example, ground bone.

14. A method as claimed in claim 12, including using grains of body-endogenous material such as, for example, ground bone.

15. A method as claimed in claim 1, wherein the step of filling the cavity with grains includes using grains that are substantially porous.

* * * * *